United States Patent
Sowden

(10) Patent No.: US 7,240,785 B2
(45) Date of Patent: *Jul. 10, 2007

(54) METHOD AND APPARATUS FOR TRANSFERRING SUBSTRATES

(75) Inventor: Harry S. Sowden, Glenside, PA (US)

(73) Assignee: McNeil-PPC, Inc., Skillman, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/045,217

(22) Filed: Jan. 28, 2005

(65) Prior Publication Data

US 2005/0126886 A1    Jun. 16, 2005

Related U.S. Application Data

(60) Division of application No. 10/393,609, filed on Mar. 21, 2003, now Pat. No. 6,880,694, which is a continuation-in-part of application No. 09/967,414, filed on Sep. 28, 2001, now Pat. No. 6,742,646.

(51) Int. Cl.
    B65G 15/42    (2006.01)

(52) U.S. Cl. .............................. 198/478.1; 198/471.1; 198/803.14

(58) Field of Classification Search ............. 198/469.1, 198/470.1, 474.1, 476.1, 803.9, 867.11, 867.12, 198/867.14, 867.15, 803.14, 803.15, 482.1, 198/471.1; 414/222.09
    See application file for complete search history.

(56) References Cited

U.S. PATENT DOCUMENTS

| 2,307,371 A | 1/1943 | Hileman |
| 2,415,997 A | 2/1947 | Eldred |
| 2,931,276 A * | 4/1960 | Zerlin .................... 198/474.1 |
| 3,300,063 A | 1/1967 | Jensen et al. |
| 3,458,968 A * | 8/1969 | Gregory, Jr. ........... 198/803.14 |
| 3,563,170 A | 2/1971 | Cvacho et al. |
| 3,567,043 A | 3/1971 | Servet et al. |
| 3,656,518 A | 4/1972 | Aronson |
| 3,726,622 A | 4/1973 | De Troyer et al. |
| 3,804,570 A | 4/1974 | Hoschele et al. |

(Continued)

FOREIGN PATENT DOCUMENTS

DE    75 35 875 U    3/1976

(Continued)

OTHER PUBLICATIONS

Catellani, et al., Int. J. Pharmaceutics, 88 (1992) 285-291, "Centrifugal die filling system in a new rotary tablet machine."

(Continued)

Primary Examiner—James R Bidwell
(74) Attorney, Agent, or Firm—David Crichton

(57) ABSTRACT

The present invention is directed to a method for transferring substrates by receiving a first substrate at a first substrate receiving station in a first transfer unit capable of holding at least two substrates, moving the first transfer unit containing only the first substrate along a conveying line to a second substrate receiving station, causing the first transfer unit to receive a second substrate at the second substrate receiving station; and transferring the first and second substrates simultaneously to a substrate transfer station.

2 Claims, 4 Drawing Sheets

U.S. PATENT DOCUMENTS

| | | | |
|---|---|---|---|
| 3,732,252 A | 8/1974 | Higuchi et al. | |
| 3,884,143 A * | 5/1975 | Ackley | 198/803.14 |
| 4,139,589 A | 2/1979 | Beringer et al. | |
| 4,273,793 A | 6/1981 | Fariel et al. | |
| 4,292,017 A | 9/1981 | Doepel | |
| 4,371,516 A | 2/1983 | Gregory et al. | |
| 4,382,422 A * | 5/1983 | Eddy et al. | 198/470.1 |
| 4,392,493 A | 7/1983 | Niemeijer | |
| 4,413,709 A | 11/1983 | Kazumi et al. | |
| 4,473,526 A | 9/1984 | Buhler et al. | |
| 4,518,335 A | 5/1985 | Pujari | |
| 4,544,345 A | 10/1985 | Buhler et al. | |
| 4,569,650 A | 2/1986 | Kramer | |
| 4,781,714 A | 11/1988 | Eckenhoff et al. | |
| 4,813,818 A | 3/1989 | Sanzone | |
| 4,820,524 A | 4/1989 | Berta | |
| 4,851,226 A | 7/1989 | Julian et al. | |
| 4,936,440 A * | 6/1990 | Focke et al. | 198/470.1 |
| 4,965,027 A | 10/1990 | Takahashi | |
| 5,059,112 A | 10/1991 | Wieser | |
| 5,073,379 A | 12/1991 | Klimesch et al. | |
| 5,075,114 A | 12/1991 | Roche | |
| 5,089,270 A | 2/1992 | Hampton et al. | |
| 5,146,730 A | 9/1992 | Sadek et al. | |
| 5,200,191 A | 4/1993 | Steele et al. | |
| 5,213,738 A | 5/1993 | Hampton et al. | |
| 5,228,916 A | 7/1993 | Berta | |
| 5,229,164 A | 7/1993 | Pins et al. | |
| 5,267,577 A * | 12/1993 | Rizzoli et al. | 198/471.1 |
| 5,415,868 A | 5/1995 | Smith et al. | |
| 5,421,447 A | 6/1995 | Ruth et al. | |
| 5,436,026 A | 7/1995 | Berta | |
| 5,451,130 A * | 9/1995 | Kempf | 198/346.2 |
| 5,456,563 A | 10/1995 | Halbo | |
| 5,459,983 A | 10/1995 | Sadek et al. | |
| 5,464,631 A | 11/1995 | Hoover et al. | |
| 5,489,436 A | 2/1996 | Hoy et al. | |
| 5,511,361 A | 4/1996 | Sauter | |
| 5,538,128 A | 7/1996 | Berta | |
| 5,609,010 A | 3/1997 | Sauter | |
| 5,641,051 A * | 6/1997 | Bergmann | 198/345.2 |
| 5,679,406 A | 10/1997 | Berta | |
| 599,865 A | 3/1998 | Richards | |
| 5,782,337 A | 7/1998 | Langland | |
| 5,795,588 A | 8/1998 | Sauter | |
| 5,824,338 A | 10/1998 | Jacobs et al. | |
| 5,830,501 A | 11/1998 | Dong et al. | |
| 5,830,502 A | 11/1998 | Dong et al. | |
| 5,834,035 A | 11/1998 | Osada et al. | |
| 5,837,301 A | 11/1998 | Arnott et al. | |
| 5,871,781 A | 2/1999 | Myers et al. | |
| 5,913,652 A * | 6/1999 | Zejda | 198/346.2 |
| 5,942,034 A | 8/1999 | Brehant et al. | |
| 5,997,905 A | 12/1999 | McTeigue et al. | |
| 6,001,391 A | 12/1999 | Zeidler et al. | |
| 6,117,479 A | 9/2000 | Hogan et al. | |
| 6,149,943 A | 11/2000 | McTeigue et al. | |
| 6,350,398 B1 | 2/2002 | Breitenbach et al. | |
| 6,405,853 B1 | 6/2002 | Cook et al. | |
| 6,742,646 B2 | 6/2004 | Sowden et al. | |
| 6,880,694 B2 * | 4/2005 | Sowden | 198/803.14 |
| 6,912,775 B1 * | 7/2005 | Pfeiffer et al. | 29/729 |

FOREIGN PATENT DOCUMENTS

| | | |
|---|---|---|
| DE | 40 25 487 A | 2/1992 |
| EP | 0 864 324 A1 | 9/1998 |
| EP | 0 963 836 A1 | 12/1999 |
| FR | 2 604 904 | 10/1986 |
| GB | 759081 | 10/1956 |
| GB | 1 227 837 A | 4/1971 |
| NL | 8602556 | 10/1986 |
| WO | 9407470 | 4/1994 |
| WO | 99/02136 | 1/1999 |
| WO | 03/020246 A1 | 3/2003 |

OTHER PUBLICATIONS

Cuff & Raouf, Pharm Tech. Jun. 1998, 96-106. "A Preliminary Evaluation of Injection Molding as a Technology to Produce Tablets."

Schmett, M., Feb. 13, 1992, "Filing Device for Mould Table of Machine for Forming Tablets," German Patent DE 4025487, Dialog File No. 351 Accession No. 8930700; Derwent World Patents Index, Abstract.

Rosato, Dominick & Donald, "Injection Molding Handbook," The Complete Molding Operation Technology, Performance, Economics (1986) pp. 189-191 & 794-795.

D'Arcy, et al., Int'l J. of Pharm, vol. 88 (1992) pp. 285-291.

Lachman, et al., Chapter II—Tablets, The Theory and Practice of Industrial Pharmacy (1986), pp. 293-345.

* cited by examiner

METHOD AND APPARATUS FOR TRANSFERRING SUBSTRATES

CROSS REFERENCE TO RELATED APPLICATION

This application is a divisional application of and claims priority to U.S. patent application Ser. No. 10/393,609 filed Mar. 21, 2003, now U.S. Pat. No. 6,880,694, which is a continuation-in-part of U.S. patent application Ser. No. 09/967,414, filed on Sep. 28, 2001, now U.S. Pat. No. 6,742,646.

FIELD OF THE INVENTION

This invention relates generally to methods and apparatuses for transferring substrates, such as tablets, from one location to another.

BACKGROUND OF THE INVENTION

Double-sided tablet presses are commonly used in the pharmaceutical industry for making tablets. Their configuration is well known. Typically, they comprise a rotor having dies located along its periphery. The rotor rotates through first and second compression zones. In each compression zone, powder is fed to dies, optionally the powder is precompressed and then compressed within the dies, and finally finished tablets are ejected from the press. Because double-sided tablet presses contain two compression zones, with each revolution of the rotor two sets of tablets are made. The tablets are ejected from opposite sides of the press at first and second tablet ejection zones. The ejected tablets are conventionally transferred away in bulk by an ejection chute leading to a collection container such as a drum or hopper.

Commonly assigned, copending U.S. patent application Ser. No. 09/967,414, the disclosure of which is incorporated herein by reference, discloses a transfer device capable of handling substrates such as tablets having a high degree of friability and softness. It is a rotating device comprising a plurality of transfer units attached to a flexible conveying means, such as a belt. It is preferably used for transferring substrates within a continuous process from one operating unit to another, for example from a compression apparatus to a coating apparatus. The flexible conveying means follows a path from the first operating unit to the second operating unit. The velocity and positions of the transfer units are synchronized with the operating units to which it is coupled, so that substrates can be smoothly captured from the first operating unit and released to the second operating unit. The transfer units comprise retainers for holding the substrates. The retainers are preferably flexible and constructed from an elastomeric material. In a preferred embodiment, the retainers are circular and comprise segmented fingers of elastomeric material.

Applicants have now designed a transfer device having transfer units comprising inner and outer, side by side retainers that sequentially rather than simultaneously capture substrates. The device may be used to transfer tablets or other substrates, preferably from a rotary, double-sided tablet press to a second location. The transfer units are mounted on a flexible conveying means that travels along a path coincident with those portions of the tablet press where tablets are ejected. In one embodiment, the transfer units are adapted to receive first tablets at a first substrate receiving station of the apparatus located proximal to the first tablet ejection zone of the tablet press, and adapted to receive second tablets at a second substrate receiving station located proximal to the second tablet ejection zone of the tablet press.

SUMMARY OF THE INVENTION

The invention provides an apparatus for transferring substrates, comprising: a) a flexible conveying means; b) a plurality of transfer units mounted to said conveying means, each transfer unit adapted to hold first and second substrates; c) a cam track defining a path from a first substrate receiving station, passing through a second substrate receiving station, and then to a substrate transfer station; and d) means for driving said conveying means along said cam track.

The invention also provides an apparatus for transferring tablets from a double-sided tablet press comprising first and second tablet ejection zones to a second location, said apparatus comprising a plurality of transfer units mounted to a flexible conveying means, each transfer unit adapted to hold first and second tablets, a cam track defining a path from a first substrate receiving station located proximal to the first tablet ejection zone, passing through a second substrate receiving station located proximal to the second tablet ejection zone, and then to a substrate transfer station located at the second location; and means for driving said conveying means along said cam track.

DETAILED DESCRIPTION OF THE INVENTION

Figure 1:
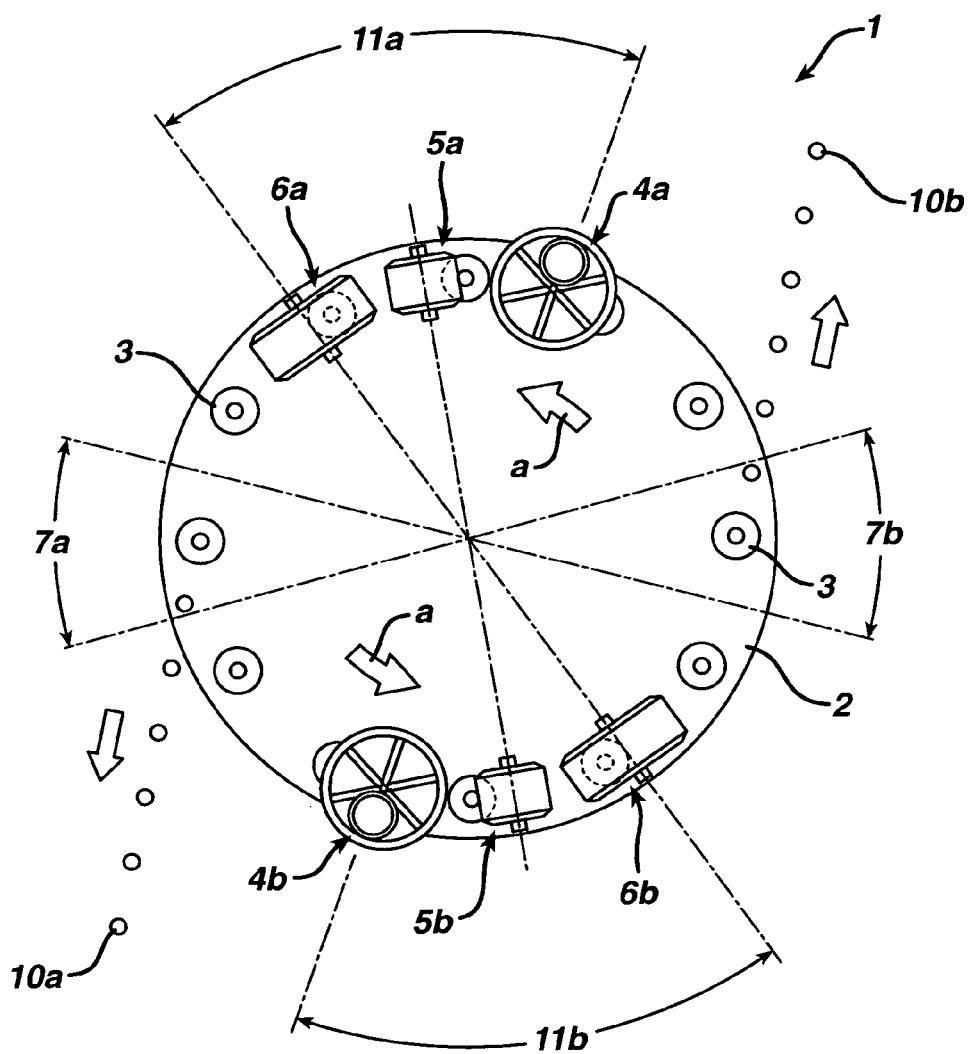
FIG. 1 depicts a conventional double-sided tablet press.

FIG. 1 depicts a conventional, double-sided tablet press 1. The tablet press 1 comprises a rotor 2 having a plurality of dies 3 around its periphery. FIG. 1 depicts 12 dies. Accordingly, each revolution of this tablet press produces 24 tablets.

Tablet press 1 comprises first and second powder feeders 4a, 4b, first and second precompression rollers 5a, 5b (which are optional), and first and second main compression rollers 6a, 6b. First powder feeder 4a is located on the opposite side of rotor 2 from second powder feeder 4b. First precompression roller 5a is located on the opposite side of rotor 2 from second precompression roller 5b. Likewise, first main compression roller 6a is located on the opposite side of rotor 2 from second main compression roller 6b. A first compression zone 11a comprises first powder feeder 4a, first precompression roller 5a and first main compression roller 6a. A second compression zone 11b comprises second powder feeder 4b, second precompression roller 5b and second main compression roller 5b. Tablets 10a, 10b are ejected from opposite sides of tablet press 1 at a first tablet ejection zone 7a and a second tablet ejection zone 7b.

The tablet press operates as follows. Powder is fed from the first powder feeder 4a to dies 3 passing thereunder as rotor 2 rotates in the direction shown by arrows a. This powder is optionally precompressed by the first precompression roller 5a, and compressed by the first main compression roller 6a into tablets 10a. Tablets 10a are ejected from the dies 3 at first tablet ejection zone 7a. Empty dies 3 next pass underneath the second powder feeder 4b and new powder is fed to the dies 3. The new powder is optionally precompressed by the second precompression roller 5b, and compressed by second main compression roller 6b into tablets 10b. Tablets 10b are ejected from the dies 3 at the second tablet ejection zone 7b.

The apparatus for transferring substrates (also referred to herein as the transfer apparatus) may be coupled with a double-sided tablet press as described above, as shown for example in FIG. 2. In particular, the transfer apparatus may be used to retrieve tablets from a double-sided tablet press and transfer them to a second location for further processing, for example coating. Advantageously, the transfer apparatus transfers the tablets on a continuous basis.

Figure 2:
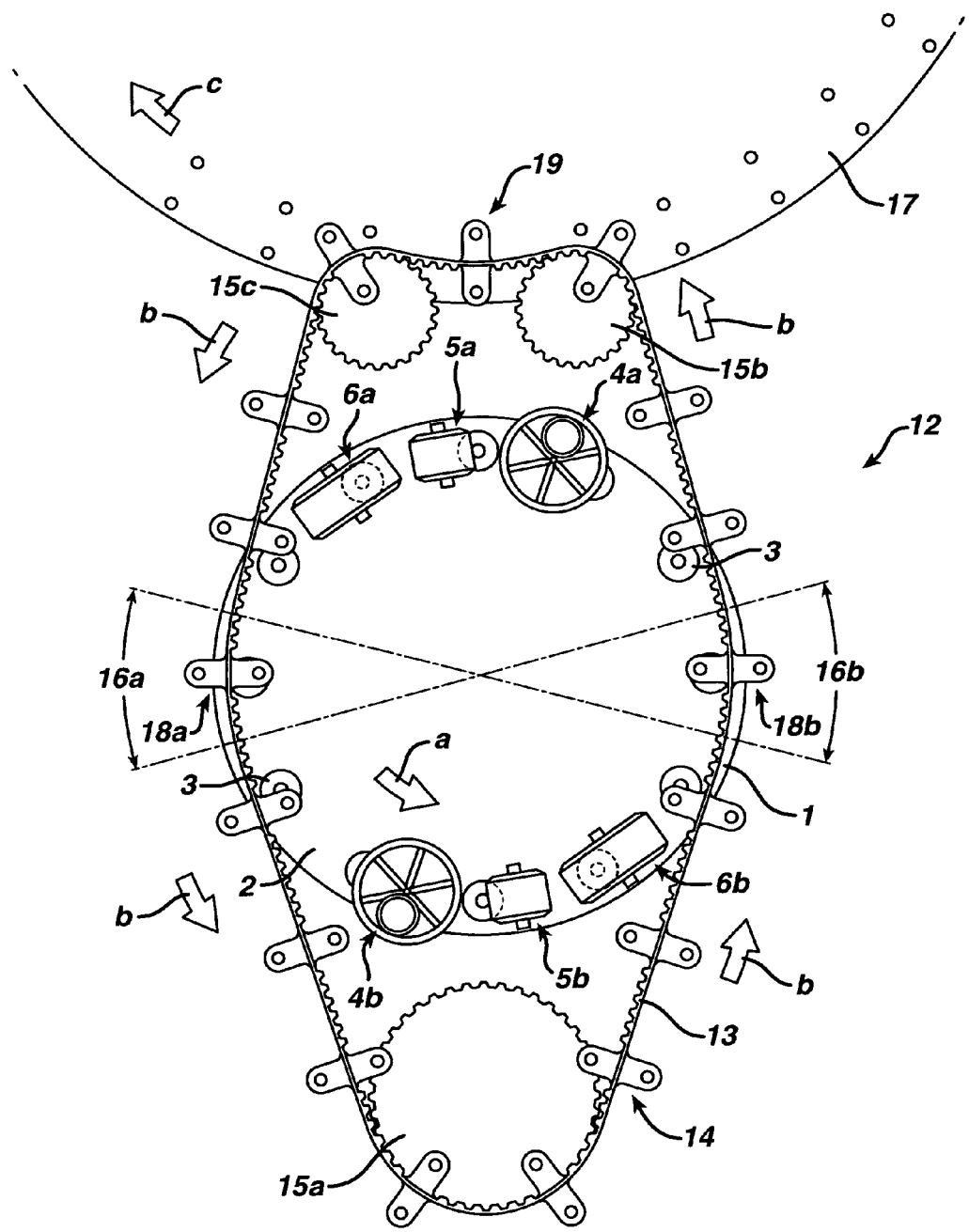
FIG. 2 depicts a transfer apparatus according to the invention coupled with the tablet press of FIG. 1.

Referring to FIG. 2, the transfer apparatus 12 comprises a flexible conveying means 13, shown here as a belt, to which a plurality of transfer units 14 are attached. The flexible conveying means may be made of any suitable material, one example of which is a composite consisting of a polyurethane toothed belt with reinforcing cords of polyester or poly-paraphenylene terephthalamide (Kevlar®, E.I. duPont de Nemours and Company, Wilmington, Del.). Other flexible materials, such as chains, linked belts, metal belts, and the like can be used as the flexible conveying means.

The transfer apparatus can be driven by any suitable power source such as an electric motor. In one embodiment, the transfer apparatus is linked to the tablet press and driven by mechanical means through a gearbox (not shown) that is connected to a main drive motor (not shown). In this configuration the velocity and positions of the individual transfer units of the transfer apparatus can be synchronized with the dies of the tablet press.

Figure 3:
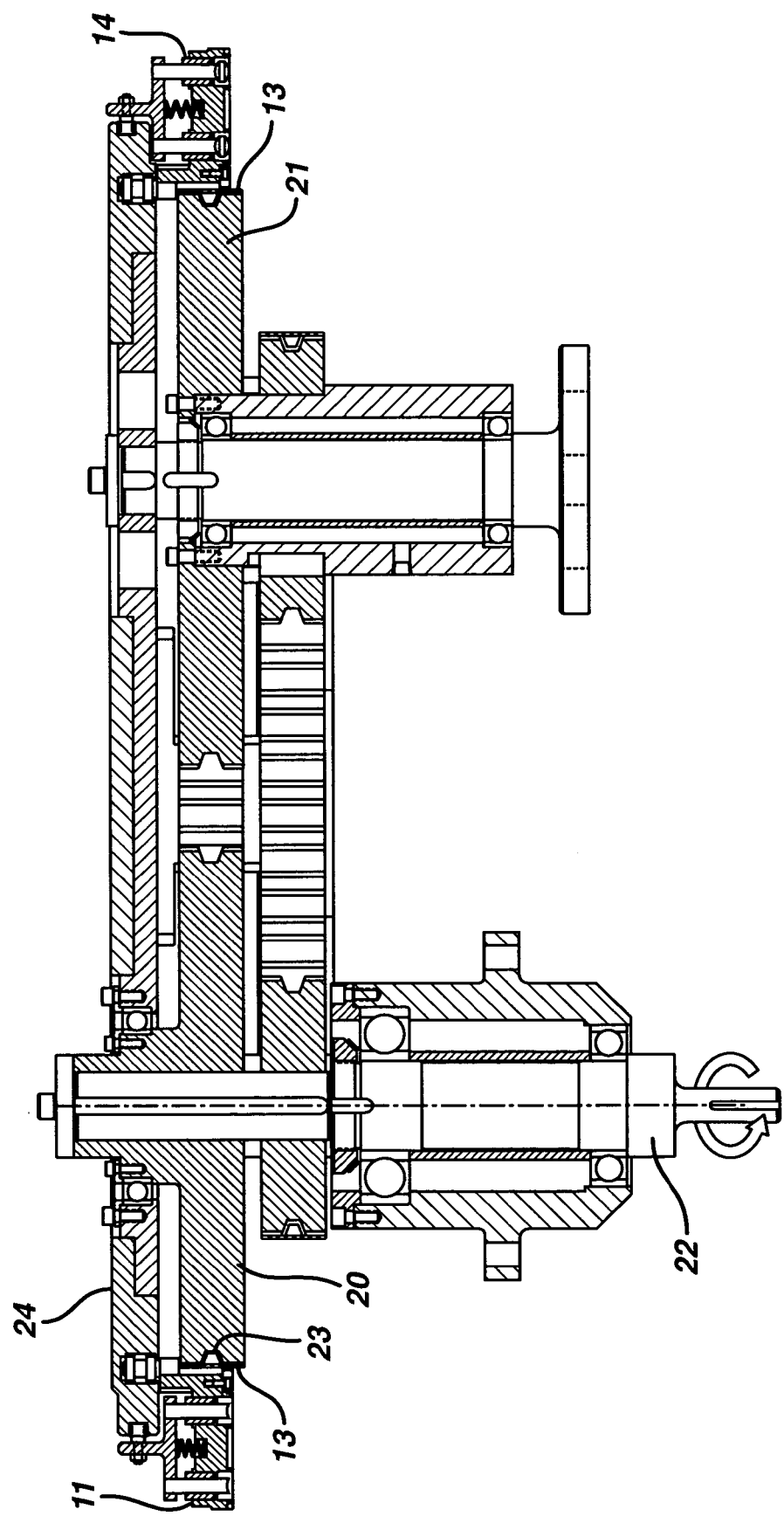
FIG. 3 is a cross-sectional view of a transfer apparatus according to the invention.

In one embodiment of the invention, as shown in FIG. 3, the transfer apparatus includes a drive pulley 20 and an idler pulley 21. A drive shaft 22 connects drive pulley 20 to a main drive train (not shown). Drive shaft 22 drives drive pulley 20 to rotate. Drive pulley 20 has teeth that engage teeth 23 disposed on the interior of flexible conveying means 13, which in turn moves the transfer apparatus in the direction of arrows b shown in FIG. 2. Idler pulley 21 has teeth that engage flexible conveying means 13 as well, which causes the idler to rotate with flexible conveying means 13.

The transfer apparatus further comprises a cam track 24 that precisely determines the path for the flexible conveying means 13. The path of cam track 24, the pitch distance between the transfer units 14, the pitch of the flexible conveying means 13, and the gear ratio between the driving means of the transfer apparatus and the driving means of the tablet press (as well as the driving means of other operating units to which the transfer apparatus is coupled) are all selected such that the transfer apparatus is precisely aligned with the tablet press and any other operating units linked to it. As each operating unit rotates, the transfer apparatus remains synchronized and phased with each, such that a precise and controlled transfer from one operating unit to another is achieved.

The velocity and positions of the transfer units 14 are matched to the velocity and positions of the dies 3 in the tablet press along two portions of the path defined by the cam track 24. As shown in FIG. 2, the path travels through a first substrate receiving station 18a, a second substrate receiving station 18b, and a substrate transfer location 19. Substrate transfer location 19 may be located for example at a second location remote from the tablet press, for instance proximal to another operating unit 17.

First portion 16a of the path defined by the cam track is an arc coincident with tablet press rotor 2 when it passes through the first tablet ejection zone 7a of the tablet press. Second portion 16b of the path is an arc coincident with the tablet press rotor 2 when it passes through the second tablet ejection zone 7b. Substrates are received along these two arc lengths.

Figure 4:
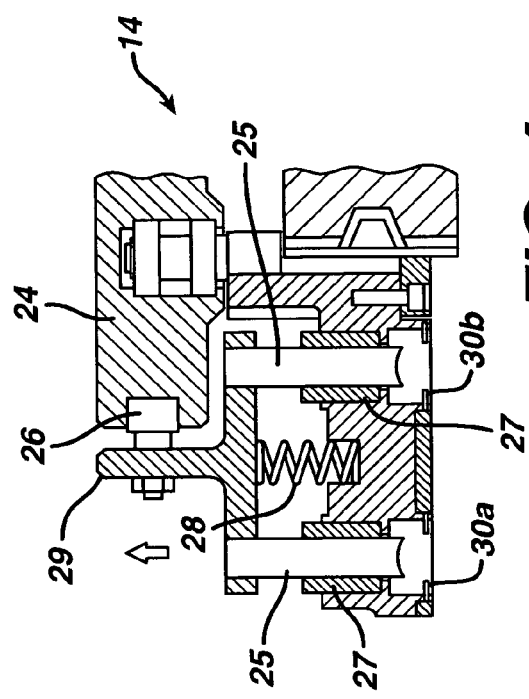

A preferred transfer unit 14 is depicted in FIG. 4. Each transfer unit is adapted to hold first and second substrates in a side-by-side fashion. Each transfer unit 14 generally includes a pair of plunger shafts 25, one or preferably more than one cam follower 26, a plurality of bearings 27 to retain the plunger shafts 25, a spring 28, a plate 29 that secures the plunger shafts 25 to cam follower 26 thereby controlling their movement, first retainer 30a and second retainer 30b. Preferably, each transfer unit 14 is attached to flexible conveying means 13 in a cantilever configuration so that retainers 30a, 30b are cantilevered over the path of the substrates.

Figure 6:
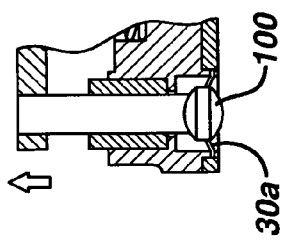
FIGS. 4–8 illustrate a preferred embodiment of a transfer unit.
Figure 7:
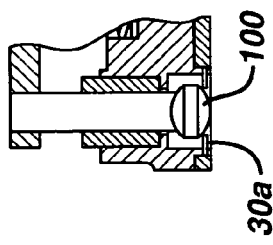
Figure 8:
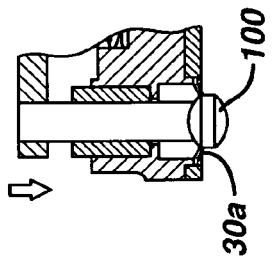
Figure 5:
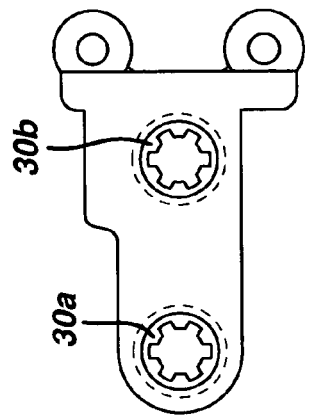

Retainers 30a, 30b are preferably flexible and constructed from an elastomeric material. Retainers 30a, 30b flex upward as shown in FIGS. 6–8 to grasp substrates, shown as tablets 100, therein. Substrates are ejected from the retainers 30a, 30b by pushing down on them, thereby flexing the retainers. Once released, the retainers 30a, 30b flex back to their original positions to receive farther substrates. In a preferred embodiment, the retainers 30a, 30b are circular and include segmented fingers of elastomeric material as shown in FIG. 5, but need not be so constructed. The retainers 30a, 30b need only be flexible enough to flex, hold a substrate, and release the substrate.

First and second retainers 30a and 30b are disposed side-by-side within each transfer unit. In one embodiment of the invention, each transfer unit is attached to the center of the flexible conveying means as shown in FIG. 2, such that the first and second retainers 30a and 30b are disposed on either side of the flexible conveying means. Viewed from the perspective of forward movement of the flexible conveying means along the path, the first retainer 30a is located on the outside of each transfer unit, while second retainer 30b is located on the inside of each transfer unit, i.e., closer to the center of the transfer apparatus. This inner/outer configuration, coupled with the path followed by the cam track, allows the transfer unit to pick up one substrate at a time, as described below.

Referring to FIG. 4, riding in cam track 24, cam follower 26 is mounted so that it can move up and down as shown in FIGS. 4–8. Plate 29 is coupled to cam follower 26. Spring 28 biases the plate 29 and cam follower 26 to an upper position. Plate 29 is also coupled to each plunger shaft 25, so that movement of the plate 29 will cause movement of the plunger shafts 25. Each plunger shaft 25 is mounted within a transfer unit 14 by a plurality of bearings 27 that permit vertical movement of the plunger shafts 25. The plunger shafts 25 are mounted so that one end of each plunger shaft 25 can move into the respective space in which a substrate is retained to eject it from the associated retainer, as shown in FIG. 8. The plunger shafts 25 and bearings 27 may be made of any suitable material.

The transfer apparatus operates as follows. As shown in FIG. 2, flexible conveying means 13 is moved along the path defined by the cam track 24 and wheels 15a, 15b, 15c in the direction of arrows b. This directs each transfer unit 14 in series to the first substrate receiving station 16a. Here, a transfer unit 14 comes into proximity with a die 3 containing a first tablet in the first tablet ejection zone 7a of the tablet press. The first retainer 30a of the transfer unit 14 aligns with the die 3. The first tablet is ejected from the die 3 by the punches of the tablet press and into the retainer 30a as shown in FIGS. 6–8. Retainer 30b remains empty.

Further rotation of the transfer apparatus by the drive pulley causes the flexible conveying means 13 and its attached transfer units 14 to travel farther along the path shown by arrows b. Retainer 30a continues to hold a first tablet therein. When the transfer unit 14 reaches the second substrate receiving station 16b it comes into proximity with a die 3 containing a second tablet in the second tablet ejection zone 7b of the tablet press. The second tablet is ejected from the die 3 and into retainer 30b. Now, retainers 30a and 30b contain first and second tablets, side-by-side in the transfer unit.

As each full transfer unit 14 reaches substrate transfer location 19, cam track 24 pushes on the cam follower 26, which pushes on plate 29. Plate 29 moves the plunger shafts 25, which in turn move down and contact the retained substrates. The substrates are pushed past the elastomeric collects and ejected from the retainers. Plunger shafts 25 return to their original upward position.

The transfer device may alternatively comprise rotatable transfer units, as described in commonly assigned, copending U.S. patent application Ser. No. 09/967,414, particularly as shown in FIGS. 77–81 therein. This is useful for example with elongated dosage forms,.i.e., caplets that are compressed horizontally but then must be coated in a vertical position. As shown in FIG. 80 of the '027 application, each transfer unit 602 comprises of a dosage form holder 608 rotatably mounted in a housing. Each dosage form holder comprises two sets of flexible retainers 630, 630B, one for entry of a substrate 630 and one for exit of a substrate 630B. During transit along path defined by the cam track 606, the dosage form holder rotates 90 degrees due to motion of a cam follower 626 within the cam track 606. An ejector pin assembly 612 enters through holes 608A in the dosage form holder 608 to eject the substrate. The dosage form holder 608 rotates 90 degrees again, returning to its horizontal position to begin the cycle over again.

The following non-limiting example further illustrates the claimed invention.

EXAMPLE

Acetaminophen-containing tablets are compressed in a double-sided tablet press, Fette model 3090. The press operates at 2000 tablets per minute per side, or 4000 tablets per minute total. The tablet press is coupled to a coating apparatus via a transfer device according to the invention. The transfer device, tablet press and coating apparatus are all driven by a common motor, and are synchronized. The transfer device comprises transfer units, each with first and second retainers, and receives acetaminophen tablets from both sides of the tablet press. The first retainer receives first tablets from one side of the tablet press, and the second retainer receives second tablets from the other side of the tablet press. The transfer units proceed to a coating apparatus, where they are ejected and coated with gelatin.

What is claimed is:

1. A method for transferring substrates which comprises in sequence:
    a) receiving a first substrate at a first substrate receiving station in a first transfer unit capable of holding at least two substrates;
    b) moving the first transfer unit containing only the first substrate along a conveying line to a second substrate receiving station;
    c) causing the first transfer unit to receive a second substrate at said second substrate receiving station; and
    d) transferring said first and second substrates simultaneously to a substrate transfer station.

2. The method of claim 1, wherein steps a) through d) are repeated as a continuous process.

* * * * *